United States Patent [19]
Kaufhold et al.

[11] Patent Number: 6,002,046
[45] Date of Patent: Dec. 14, 1999

[54] PROCESS FOR THE PREPARATION OF CYCLOPROPYL ALKYL KETONES

[75] Inventors: Manfred Kaufhold, Marl; Wolfgang Kleemiss, Haltern; Udo Jegelka, Recklinghausen; Michael Korell, Bochum, all of Germany

[73] Assignee: Huels Aktiengesellschaft, Marl, Germany

[21] Appl. No.: 09/263,876

[22] Filed: Mar. 8, 1999

[30] Foreign Application Priority Data

Mar. 6, 1998 [DE] Germany .................. 198 09 775

[51] Int. Cl.$^6$ .................................. C07C 45/54
[52] U.S. Cl. .................. 568/343; 568/347; 568/361; 549/507
[58] Field of Search .................. 568/343, 347, 568/361; 549/507, 513

[56] References Cited

U.S. PATENT DOCUMENTS

| | | | |
|---|---|---|---|
| 5,254,739 | 10/1993 | Hunston et al. | 568/346 |
| 5,629,455 | 5/1997 | Kaufhold et al. | 568/343 |
| 5,763,627 | 6/1998 | Kaufhold | 549/507 |

Primary Examiner—Shailendra Kumar
Assistant Examiner—Sreeni Padmanabhan
Attorney, Agent, or Firm—Oblon, Spivak, McClelland, Maier & Neustadt, P.C.

[57] ABSTRACT

Cyclopropyl alkyl ketones are separated from 3-acyltetrahydrofuran-2-ones by adding an alcohol, water or a water/alcohol mixture to a reaction product containing $C_{1-4}$-alkyl cyclopropyl ketone and 4,5-dihydro-2-alkylfuran by-product and an acid catalyst and reacting the by-product with the added alcohol, water of water/alcohol mixture before, during or after distilling said reaction product; and effectively separating $C_1$-$_4$-alkyl cyclopropyl ketone from reaction by-products.

In the preparation of cyclopropyl alkyl ketones from 3-acyltetrahydrofuran-2-ones very reactive 4,5-dihydro-2-alkylfurans are also produced. By reacting such compounds with nucleophilic compounds, such as alcohols or water, before, during or after distillation of the reaction products, it is possible reliably to separate off the 4,5-dihydro-2-alkylfurans as high-boiling addition compounds. The offgas which is produced in the production process for cyclopropyl alkyl ketones can be simply and reliably purified by reactive washing. The byproducts, which are difficult to handle for a production process, can thus be reliably eliminated.

15 Claims, No Drawings

PROCESS FOR THE PREPARATION OF CYCLOPROPYL ALKYL KETONES

BACKGROUND OF THE INVENTION

1. Field of the Invention

The present invention relates to a process for the preparation of cyclopropyl alkyl ketones containing $C_1$- to $C_4$-alkyl groups from 3-acyltetrahydrofuran-2-ones.

2. Description of the Background

Cyclopropyl ketones are important intermediates for the preparation of pharmaceuticals and agrochemicals.

They are prepared by a reaction as shown in the following equation:

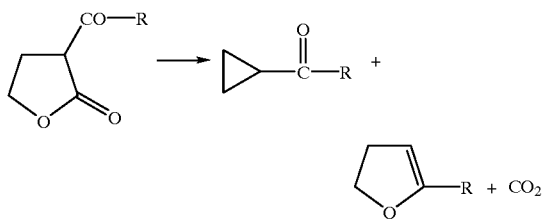

4,5-Dihydro-2-alkylfurans and carbon dioxide are byproducts of the reaction.

Processes for the preparation of cyclopropyl alkyl ketones are known as disclosed in EP-A-O 552 586 and EP-A-O 725 066. These processes involve reacting 3-acyltetrahydrofuran-2-one with alkali metal halide at a temperature from 160–220° C., and then distilling and condensing cyclopropyl alkyl ketone and the byproduct 4,5-dihydro-2-alkylfuran.

In the preparation of cyclopropyl methyl ketone (CPMK) from 3-acetyltetrahydrofuran-2-one and acetylbutyrolactone (ABL), 4,5-dihydro-2-methylfuran (DHMF) is produced in amounts of, in most cases, from 5–30%, based on the total amount of CPMK and DHMF. In order to obtain high-purity CPMK, the mixture of CPMK and DHMF must be fractionated. German patent Application No. P 197 10 879.2 thus describes a continuous process for the removal of DHMF by distillation. This process, however, requires a rectification column which has a high separation efficiency.

In addition, DHMF is a compound which, according to Houben-Weyl, Methoden der Organischen Chemie, Volume VI/3, 1965, p. 698, can react vigorously with nucleophiles in the presence of traces of acid with the release of large amounts of heat. In the preparation of CPMK on a commercial scale, the handling of such a reactive byproduct as DHMF is thus undesirable. This is because improper handling of DHMF or of a DHMF-containing fraction may be injurious for humans and the environment. A need, therefore, continues to exist for an improved method of producing CPMK which effectively separates DHMF while avoiding risk of contact with DHMF.

SUMMARY OF THE INVENTION

Accordingly, one object of the present invention is to provide a method of separating 4,5-dihydro-2-alkylfuran from a CPMK reaction product which is technically simple and effective and which permits safe handling and disposal of the separated by-product.

Briefly, this object and other objects of the present invention as hereinafter will become more readily apparent can be attained by a process, comprising:

adding an alcohol, water or a water/alcohol mixture to a reaction product containing $C_{1-4}$-alkyl cyclopropyl ketone and 4,5-dihydro-2-alkylfuran by-product and an acid catalyst and reacting the by-product with the added alcohol, water of water/alcohol mixture before, during or after distilling the reaction product; and effectively separating $C_{1}$-$_4$-alkyl cyclopropyl ketone from reaction by-products.

DETAILED DESCRIPTION OF THE PREFERRED EMBODIMENTS

The surprising feature of the present invention is that the present method makes it possible to substantially react 4,5-dihydro-2-alkylfuran by-product at a high rate with water or alcohol and then to separate CPMK from the reaction product without problems. The heat liberated from the reaction is absorbed by an excess of trapping medium comprising alcohol, water or alcohol/water mixtures and is thus dissipated in a controlled manner. This absorption of heat is particularly required if the reaction is conducted in the homogeneous phase.

The excess of trapping medium can be large as desired. For cost reasons, the weight ratio of 4,5-dihydro-2-alkylfuran to trapping medium is in most cases from 1:2–1:50, preferably from 1:5–1:30.

DHMF is particularly reactive toward water. In order reliably to avoid the formation of two phases during the reaction of DHMF with water, mixtures of water with alcohols are preferably used. The water content of the mixtures is frequently at most 40% by weight and is preferably only at most 20% by weight. Preference is also given to anhydrous alcohols. Examples of suitable alcohols are ethanol, isopropanol, n-propanol, n-butanol, pentanol, hexanol, 2-ethylhexanol, nonanol, decanol and also polyhydric alcohols, such as ethylene glycol and glycerol. Preference is given to alcohols having a boiling point of from 100–300° C.

Based on the total amount of water and alcohol, the media used for the reaction with the 4,5-dihydro-2-alkylfurans may also comprise up to 20% by weight of other organic solvents, such as ketones, ethers or esters.

Although in the case of the cyclopropyl alkyl ketones, ethyl, isopropyl and butyl are also suitable alkyl groups, preference is given according to the invention to methyl groups. Thus, ABL is preferably converted into CPMK and DHMF.

The trapping media also preferably contain up to 15% by weight of carboxylic, sulfonic or mineral acids, based on the total amount of water and alcohols, as catalysts. The content is particularly preferably less than 10% by weight, and amounts of from 1–6% by weight are very particularly preferred. Acidic ion exchangers and acidic minerals, such as, for example, alumosilicates, can also be used.

Examples of suitable carboxylic acids are acetic acid, propionic acid, maleic acid, fumaric acid, succinic acid, adipic acid, p-toluenesulfonic acid and methanesulfonic acid.

Mineral acids mentioned here are merely hydrochloric acid, sulfuric acid and phosphoric acid.

The reaction is carried out in most cases at temperatures of from 10–80° C.

If the trapping medium, a nucleophilic reactant, is added prior to purification distillation, distillation produces a cyclopropyl alkyl ketone without a preliminary fraction comprising 4,5-dihydro-2-alkylfuran.

Cyclopropyl alkyl ketones and 4,5-dihydro-2-alkylfurans and in particular CPMK and DHMF are relatively volatile compounds which, in practice, can only be eliminated quantitatively during the reaction at considerable effort by condensation. In most cases, therefore, the offgas, which largely consists of carbon dioxide, and also cyclopropyl alkyl ketones and 4,5-dihydro-2-alkylfurans, is present in such amounts that it cannot be released without prior purification.

Although, according to Ullmann's Encyclopedia of Industrial Chemistry, 5th Ed., Vol. B3, p. 8-7 ff and p. 9–41 ff, offgases can be purified by adsorption, for example on activated carbon, or by absorption in a liquid, this results, however, in the problem of disposal of the loaded adsorbent or absorbent, not least because, in the present case, products having very different chemical and physical properties are to be removed and one of the substances is of significance from a safety point of view and can lead to deflagration or explosion.

In addition, it is also a problem that carbon dioxide is formed in large amounts, indeed in stoichiometric amounts according to the equation given above. Exploitation of the physical solubility of ketones and dihydrofurans is frequently inadequate here to separate off sufficient of said constituents. Moreover, due to the large amounts of carbon dioxide, removal by aqueous alkaline washing is impossible since this produces considerable amounts of salt.

The novel process is also successfully applied to the offgas of the reaction in which cyclopropyl alkyl ketones are prepared from 3-acyltetrahydrofuran-2-ones. Here, the acid-catalyzed reaction with the alcohols, water or alcohol/water mixtures is carried out as a reactive wash.

The excess of washing liquid compared with the compounds to be separated off can be as large as desired during offgas purification.

The offgas is advantageously purified in two stages. In a first stage, more than 50% of the 4,5-dihydro-2-alkyl-furan is separated off using alcohols, water or alcohol/water mixtures. The second stage then involves washing with sulfuric acid.

According to the process of the invention, the washing liquid used in the second stage is from 60–100% strength, preferably from 70–100% strength, sulfuric acid. Sulfuric acid, in particular, is able to extract the remaining amounts of cyclopropyl alkyl ketone and 4,5-dihydro-2-alkylfuran from the off-gas from the first washing stage in virtually quantitative amounts.

Regardless of the amounts of degradation products of washed-out organic compounds present, the wash sulfuric acid can then be used without problems as a raw material in a customary preparation process for obtaining sulfuric acid, and the sulfuric acid present can thus be recovered in an environmentally friendly manner.

The reactive wash with the alcohol or alcohol/water mixture is generally carried out at a temperature from 15–70° C., and the wash with sulfuric acid at a temperature from 10–50° C.

The process of the invention makes it possible to convert 4,5-dihydro-2-alkylfurans reliably and with controlled release of the heat of reaction into addition products and to separate these compounds in virtually quantitative amounts.

The organic media which are preferably used can be disposed of by combustion utilizing thermal energy. Since, in this case, high requirements are not placed on the purity of the liquid used, it is also possible to use suitable waste products from other production processes, for example, intermediate fractions of suitable composition, possibly containing water, which are not very economically attractive.

Having generally described this invention, a further understanding can be obtained by reference to certain specific examples which are provided herein for purposes of illustration only and are not intended to be limiting unless otherwise specified.

EXAMPLES

EXAMPLE 1

A mixture of 97.0 g (1.15 mol) of 4,5-dihydro-2-methylfuran (DHMF), 483.6 g (5.75 mol) of cyclopropyl methyl ketone (CPMK) and 1.0 g of montmorillonite K 10 (Südchemie, D-80333 Munich) is stirred at 25° C. A 71.5 g (1.15 mol) amount of ethylene glycol is slowly added to the mixture. A reaction temperature of at most 30° C. is maintained. The mixture is stirred for a further 1 h and the catalyst is then removed by filtration. A 2 g amount of sodium carbonate is added to the mixture, which is then fractionated over a 0.5 m Multifil column under atmospheric pressure. During distillation, a bottom temperature of 200° C. is not exceeded until an initial fraction of 435.2 g (90%) of CPMK having a GC purity of >99% is obtained.

EXAMPLE 2

A mixture of 195.0 g (2.3 mol) of CPMK, 38.7 g (0.46 mol) of DHMF and 1.0 g of montmorillonite K 10 is stirred at 25° C. A 29.2 g (0.46 mol) amount of ethylene glycol is metered in, during which the temperature rises to 40° C. The mixture is stirred for a further 1 h, the acid catalyst is removed by filtration and 2 g of sodium carbonate are added to the mixture. The mixture is then fractionated over a 0.5 m Multifil column at a pressure of about 100 mbar. At a bottom temperature of at most 80° C. and without an initial fraction, 168.5 g (85%) of CPMK having a GC purity of >98% are obtained.

EXAMPLE 3

A mixture of 360.0 g of butanol and 40.0 g of 10% strength aqueous sulfuric acid is introduced into a reaction calorimeter (Mettler RC-1) at 25° C. with stirring. DHMF is introduced at a rate of 160.0 g/h for 0.5 h, the heat of the reaction produced/time being compared at all times with the amount of heat/time expected in theory (under adiabatic conditions, the heat of the reaction of DHMF with butanol/10% sulfuric acid has previously been determined as 40 kJ/mol) The two amounts of heat/time (20 J/s) agree at any given time. When DHMF is introduced, there is thus a momentary reaction of DHMF to DHMF addition products.

EXAMPLE 4

A 400.0 g amount of 50% strength aqueous acetic acid is introduced into a reaction calorimeter (Mettler RC-1) at 25° C. with stirring. DHMF is introduced at a rate of 160.0 g/h for 0.5 h, the heat of the reaction produced/time being compared at all times with the amount of heat/time expected in theory (under adiabatic conditions, the heat of the reaction of DHMF with 50% strength acetic acid has previously been determined as 40 kJ/mol). The two amounts of heat/time (20 J/s) agree at any given time. When DHMF is introduced, there is thus a momentary reaction of DHMF to DHMF addition products.

EXAMPLE 5

An off-gas stream of 350 liters/h of carbon dioxide containing 17 g/m$^3$ of CPMK and 34 g/m$^3$ of DHMF is introduced to the bottom of a column 300 mm in length and 30 mm in diameter at a temperature of 25° C. The packing in the column is 200 mm Raschig rings (diameter 6 mm). The washing medium, 260 g of a mixture of 2-ethyl-hexanol containing 1.35% of adipic acid, is drawn off at the bottom of the column via a circulating pump at a circulation rate of 12 l/h and reintroduced at the top. The gas mixture leaving the washing column contains 5.4 g/m$^3$ of CPMK and 11.2 g/m$^3$ of DHMF and is introduced into 500 g of concentrated sulfuric acid (100% strength) via a glass frit.

At the outlet of this two-stage washing combination, no organic constituents were determined in the gas phase over a period of 16 h.

EXAMPLE 6

The experiment is conducted as described in Example 5, although the washing medium used for the first stage is 260 g of a mixture of ethylene glycol containing 5% of p-toluenesulfonic acid. The loading after the first wash is 6.5 g/m$^3$ of CPMK and 6.7 g/m$^3$ of DHMF. After the second wash again no loading can be detected.

The disclosure of priority German Application No. 198 09 775.1 filed Mar. 6, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process, comprising:
    adding an alcohol, water or a water/alcohol mixture to a reaction product containing $C_{1-4}$-alkyl cyclopropyl ketone and 4,5-dihydro-2-alkylfuran by-product and an acid catalyst and reacting the by-product with the added alcohol, water or water/alcohol mixture before, during or after distilling said reaction product; and
    effectively separating $C_{1-4}$-alkyl cyclopropyl ketone from reaction by-products.

2. The process as claimed in claim 1, wherein the weight ratio of 4,5-dihydro-2-alkylfuran to alcohol, water or alcohol/water mixture ranges from 1:2–1:50.

3. The process as claimed in claim 2, wherein said weight ratio ranges from 1:5–1:30.

4. The process as claimed in claim 1, wherein the alcohol/water mixture has a water content of up to 40% by weight.

5. The process as claimed in claim 1, wherein the alcohol has a boiling point ranging from 100–300° C.

6. The process as claimed in claim 1, wherein in the preparation of cyclopropyl methyl ketone, the 4,5-dihydro-2-methylfuran is separated from 3-acetyltetrahydrofuran-2-one.

7. The process as claimed in claim 1, wherein the catalyst is up to 15% by weight of carboxylic acid, sulfonic acid or mineral acid, based on the total amount of alcohol and/or water.

8. The process as claimed in claim 7, wherein from 1–6% by weight of carboxylic acid, sulfonic acid or mineral acid is present.

9. The process as claimed in claim 1, wherein the catalyst is an acidic ion exchanger or mineral acid.

10. The process as claimed in claim 1, wherein the mineral acid is sulfuric acid, hydrochloric acid or phosphoric acid.

11. The process as claimed in claim 1, wherein the mineral acid is sulfuric acid.

12. The process as claimed in claim 1, wherein the by-product is subjected to the reaction in the form of a reactive wash before, during or after distillation of the reaction products.

13. The process as claimed in claim 12, wherein, in a first stage, more than 50% of the 4,5-dihydro-2-alkylfurans are removed by reactive washing with alcohol or alcohol/water mixture, and, in a second stage, the furans are washed with from 60–100% strength sulfuric acid.

14. The process as claimed in claim 12, wherein the wash sulfuric acid is 70–100% strength sulfuric acid.

15. The process as claimed in claim 1, wherein the alcohol is ethanol, isopropanol, n-propanol, n-butanol, pentanol, hexanol, 2-ethylhexanol, nonanol, decanol or a polyhydric alcohol.

* * * * *